(12) United States Patent
McCrory et al.

(10) Patent No.: US 6,333,971 B2
(45) Date of Patent: Dec. 25, 2001

(54) FIDUCIAL MARKER

(75) Inventors: Jennifer J. McCrory, Lincoln, RI (US); J. Michael Fitzpatrick, Nashville, TN (US); M. Robert Willcott, Nashville, TN (US); Robert J. Maciunas, Nashville, TN (US); Calvin R. Maurer, Jr., Nashville, TN (US); George S. Allen, 628 Westview Ave., Nashville, TN (US) 37205

(73) Assignee: George S. Allen, Nashville, TN (US)

( * ) Notice: Subject to any disclaimer, the term of this patent is extended or adjusted under 35 U.S.C. 154(b) by 0 days.

(21) Appl. No.: 09/742,411

(22) Filed: Dec. 22, 2000

Related U.S. Application Data (62) Division of application No. 08/480,709, filed on Jun. 7, 1995.

(51) Int. Cl.⁷ .................................................. H05G 1/28
(52) U.S. Cl. ................................. 378/162; 600/7; 600/8; 424/9.3; 424/9.4
(58) Field of Search .................................. 378/162, 163, 378/164, 170, 204, 205; 600/7, 8; 606/130; 424/9.3–9.455

(56) References Cited

U.S. PATENT DOCUMENTS

| | | | |
|---|---|---|---|
| 3,836,776 | 9/1974 | Gullekson | 250/312 |
| 4,310,507 | 1/1982 | Luckey | 424/4 |
| 4,583,538 | 4/1986 | Onik et al. | 128/303 B |
| 4,608,977 | 9/1986 | Brown | 128/303 B |
| 4,612,930 | 9/1986 | Bremer | 128/303 B |
| 4,615,876 | 10/1986 | Troutner et al. | 424/1.1 |
| 4,615,879 | 10/1986 | Runge et al. | 424/9 |
| 4,618,978 | 10/1986 | Cosman | 378/164 |
| 4,662,887 | 5/1987 | Turner et al. | 623/16 |
| 4,669,481 | 6/1987 | Eisenberg et al. | 128/654 |
| 4,675,173 | 6/1987 | Widder | 424/9 |
| 4,728,575 | 3/1988 | Gamble et al. | 428/402.2 |
| 4,729,892 | 3/1988 | Beall | 424/9 |
| 4,760,173 | 7/1988 | Klaveness | 562/449 |
| 4,826,487 | 5/1989 | Winter | 606/130 |
| 4,860,331 | 8/1989 | Williams et al. | 378/163 |
| 4,927,624 | 5/1990 | Bryant et al. | 424/9 |

(List continued on next page.)

FOREIGN PATENT DOCUMENTS

| | | |
|---|---|---|
| 0 146 699 | 7/1985 | (EP) . |
| 0 427 358 | 5/1991 | (EP) . |
| 0 591 712 | 4/1994 | (EP) . |

OTHER PUBLICATIONS

Proceedings of the Meeting of the American Society for Stereotactic and Functional Neurosurgery, Pittsburgh, PA., Jun. 16–19, 1991, Stereotact Funct Neurosurg 1992; 58:103–107, 1992 S. Karger AG, Basel; by R.J. Maciunas, et al.: An Independent Application Accuracy Evaluation of Stereotactic Frame Systems.

Chapter 14 of Magnetic Resonance Imaging, Second Edition, David D. Stark, et al., Mosby Publishing, St. Louis, 1992.

J. Rousseau, et al., "A frameless method for 3D MRI– and CT– guided stereotaxic", European Radiology, vol. 2, No. 1, pp. 35–41, 1992.

(List continued on next page.)

*Primary Examiner*—David P. Porta
(74) *Attorney, Agent, or Firm*—Kenyon & Kenyon (57) ABSTRACT

An implantable fiducial marker having a sealed cavity for the introduction of an imaging agent that provides imaging capability in several modes, including Computed Tomographic imaging (CT) and Magnetic Resonance Imaging (MRI) is disclosed. The marker may be permanent, or it may be temporary and readily detachable from its anchor site. Combinations or agents imageable under CT scanning are combined with agents imageable under MRI scanning.

23 Claims, 6 Drawing Sheets

U.S. PATENT DOCUMENTS

| | | | |
|---|---|---|---|
| 4,989,608 | 2/1991 | Ratner | 128/653.2 |
| 4,991,579 | 2/1991 | Allen | 128/653 |
| 5,016,639 | 5/1991 | Allen | 128/653.1 |
| 5,019,370 | 5/1991 | Jay et al. | 424/4 |
| 5,023,072 | 6/1991 | Cheng | 424/9 |
| 5,046,498 | 9/1991 | Fishman | 128/653 |
| 5,055,288 | 10/1991 | Lewis et al. | 424/9 |
| 5,099,846 | 3/1992 | Hardy | 128/653.1 |
| 5,120,527 | 6/1992 | Li et al. | 424/9 |
| 5,138,165 | 8/1992 | Petroff | 250/363 |
| 5,142,930 | 9/1992 | Allen et al. | 74/469 |
| 5,178,146 | 1/1993 | Giese | 128/653.2 |
| 5,211,166 | 5/1993 | Sepponen | 128/653.5 |
| 5,368,030 | 11/1994 | Zinreich et al. | 600/414 |
| 5,394,457 * | 2/1995 | Leibinger et al. | 378/162 |
| 5,401,489 * | 3/1995 | Born et al. | 424/9.3 |
| 5,469,847 | 11/1995 | Zinreich et al. | 600/414 |
| 5,817,289 * | 10/1998 | Klaveness et al. | 424/9.4 |

OTHER PUBLICATIONS

D. Roberts, et al., "A frameless sterotaxic integration of computerized tomographic imaging and the operating microscope", J. Neurosurgery, vol. 65, pp. 545–549, Oct., 1986.

J. Rousseau, et al., "Validation of a New Method for Stereotactic Localization using MR Imaging", J. Comput Assist Tomoge, vol. 15, No. 2, pp. 291–296, 1991.

P. Clarysse, et al., A Computer–Assisted System for 3–D Frameless Localization in Stereotaxic MRI, IEEE Transactions on Medical Imaging, vol. 10, No. 4, pp. 523–529, Dec. 1991.

R. Oberleitner, et al. "Plating/Mesh Systems Leibinger's Technical Developments for Skull Bass Surgery," pp. 293–304, I, Janecka, et al., Skull Base Surgery Anatomy, Biology and Technology.

S. Bushong, Magnetic Resonance Imaging Physical and Biological Principles, 28 pages.

Journal of Computer Assisted Tomography, Mar./Apr. 1985, vol. 9, No. 2, 1985, Raven Press, New York, E.E. Babcock: Edge Artifacts in MR Images: Chemical Shift Effect.

AJR 154, Jun. 1990,, A.S. Smith, et al.: Intracranial Chemical–Shift Artifacts on MR Images of the Brain: Observations and Relation to Sampling Bandwidth, pp. 1275–1283.

AJR, vol. 145, Jul. 1985, J.C. Weinreb, et al.: Chemical Shift Artifact in Clinical Magnetic Resonance Imagings at 0.35 T, pp. 183–185.

Radiology, vol. 181, No. 1, Oct. 1991, R.C. Smith, et al.: Chemical Shift Artifact: Dependence on Shape and Orientation of the Lipid–Water Interface[1], pp. 225–229.

Radiology, vol. 158, No. 2, Feb. 1986; Pituitary Fossa: Chemical Shift Effect in MR Imaging[1], pp. 461–462.

Radiology, vol. 153, No. 3, Dec. 1984: Chemical Shift Misregistration Effect in Magnetic Resonance Imaging[1], pp. 819–820.

* cited by examiner

FIDUCIAL MARKER

This application claims the priority benefit of 08/017,167, filed Feb. 12, 1993. The present application is a divisional of 08/480,709, filed Jun. 7, 1995, which is in turn a Continuation of 08/017,167, filed Feb. 12, 1993.

BACKGROUND OF THE INVENTION

Recent years have seen the development of diagnostic techniques that allow the practicing clinician to obtain high fidelity views of the anatomical structure of the human body. Imaging systems such as computed tomographic (CT) x-ray imagers, positron emission tomographic (PET) scanners, single photon emission computed tomography (SPECT) scanners and nuclear magnetic resonance imaging (MRI) machines have provided clinicians with the ability to improve visualization of the anatomical structure of the human body without surgery or other invasive techniques. In lieu of exploratory surgery, the patient can be subjected to the scanning modalities of such imaging systems, and the patient's anatomical structure can be reproduced in a form for evaluation by a trained doctor.

The doctor sufficiently experienced in these techniques can evaluate the images of the patient's anatomy and determine if there are any abnormalities present. An abnormality in the form of a lesion appears on the image as a shape that has a discernable contrast with the surrounding area. The difference in contrast is due to the lesion having imaging properties that differ from those of the surrounding body tissue. Moreover, the contrasting shape that represents the lesion appears at a location on the image where such a shape would not normally appear with regard to a similar image of a healthy person.

Once a lesion has been identified, several methods of treatment are utilized to remove or destroy the lesion, including chemotherapy, radiation therapy, and surgery. When chemotherapy is chosen, drugs are introduced into the patient's body to destroy the lesion. During the course of treatment, imagers are commonly used to follow the progress of treatment by subjecting the patient to periodic scans and comparing the images taken over the course of the treatment to ascertain any changes in the lesion configurations.

In radiation therapy, the images of the lesion generated by the imager are used by a radiologist to adjust the irradiating device and to direct radiation solely at the lesion while minimizing or eliminating adverse effects to surrounding healthy tissue. During the course of the radiation treatment, the imaging system is also used to follow the progress of the patient in the same manner described above with respect to chemotherapy.

When surgery is used to remove a lesion or other abnormality, the images of the lesion in the patient can guide the surgeon during the operation. By reviewing the images prior to surgery, the surgeon can decide the best strategy for reaching and biopsying, excising, or otherwise manipulating the abnormality or lesion, whether it is a brain tumor, arteriovenous malformation, infection or other entity. After surgery has been performed, further scanning is utilized to evaluate the success of the surgery and the subsequent progress of the patient.

A problem associated with the scanning techniques mentioned above concerns the accurate selection and comparison of views of identical areas in images that have been obtained by imagers at different times or by images obtained essentially at the same time using different image modalities, e.g., CT, MRI, SPECT, and PET. This problem has two aspects. First, in order to relate the information in an image of the anatomy to the anatomy itself, it is necessary to establish a one-to-one mapping between points in the image and points on the anatomy. This is referred to as registering image space to physical space.

The second aspect concerns the registration of one image space to another image space. The goal of registering two arbitrarily oriented three dimensional images is to align the coordinate systems of the two images such that any given point in the scanned anatomy is assigned identical addresses in both images. The calculation of the rigid body transformation necessary to register the two coordinate systems requires knowledge of the coordinate vectors of at least three points in the two systems. Such points are called "fiducial points" or "fiducials," and the fiducials used are the geometric centers of markers, which are called "fiducial markers". These fiducials are used to correlate image space to physical space and to correlate one image space to another image space. The fiducial markers provide a constant frame of reference visible in a given imaging mode to make registration possible. The general technique for using fiducial markers to obtain registration of image data across time is set forth in U.S. Pat. No. 4,991,579 to George S. Allen, the contents of which are incorporated herein by reference.

One problem extant in the field lies in the provision of fiducials capable of use with several imaging modalities. MRI and X-ray CT images are digital images, in which the images are formed point by point. These points are called picture elements, or pixels, and are associated with an intensity of light emitted from a cathode ray tube, or are used to form an image on film. The array of lighted pixels enables the observer to view an image. The manner in which the intensity of any given pixel is altered or modulated varies with the imaging modality employed. In X-ray CT, such modulation is a function primarily of the number of electrons per unit volume being scanned. In MR imaging, the parameters primarily influencing this modulation are the proton spin density and longitudinal and transverse relaxation times T1 and T2, which are also known as the spin-lattice and spin-spin relaxation times, respectively. In constructing a fiducial marker, one must be aware that an agent that can be imaged under one imaging modality will not necessarily be imageable under another modality. And yet, the ability to image under both CT and MRI with a given marker would be especially useful, in that one would then be able to register images derived from different imaging modalities. For example, the capability to register CT and MR images would allow the integration of information concerning bony structure provided by a CT scan with the soft tissue anatomical information provided by an MRI scan. There remains a need for a fiducial marker that can be used to establish a known coordinate system under several imaging modalities.

A further problem in the field arises from the competing needs of accommodating patient comfort, which would tend to lead clinicians toward the minimization of marker size, with the desire of clinicians to use markers that are as bright and thus as large as possible. Such brightness is desirable because it provides a strong signal that can be distinguished from noise inherent in the imaging process. The use of large-sized markers is also desirable so that the image of the marker occupies as many pixels as possible. Increasing the number of pixels occupied by the marker increases the accuracy with which the position of the marker can be determined. Furthermore, the general technique of using fiducial markers requires the determination of the centroid of the marker; it is easier to compute the centroid for a large, bright marker than for a smaller, dimmer marker. On the other hand, the larger the marker is, the more difficult it is for the patient to tolerate its presence for extended periods of time. There remains a need for a marker which can exploit the advantages presented by increased size that would also be tolerated by the patient during the period of its use. There is also a need for a small multi-modality marker that can be implanted into a patient and remain there for more extended periods of time. Such a more permanent fiducial marker would preferably be detectable by a non-invasive technique so that its position in physical space could be determined and its centroid computed even as it remained hidden from visual inspection beneath the patient's skin.

SUMMARY OF THE INVENTION

In view of the foregoing needs, the present invention provides medical workers with fiducial markers that can be imaged under a variety of imaging modalities, i.e., are multi-modal. The markers can be used to register image space onto image space across imaging modalities. The fiducial marker may also be used for the registration of imaging space and physical space for the successful performance of image guided craniotomies, biopsies, cyst aspirations, radiation therapy, ventricular shunt placements, and other similar surgeries.

A fiducial marker having features of the present invention includes a hollow container, preferably cylindrical or spherical, that may be made of imageable material and which is filled with liquids suitable for various imaging modalities. In one version, the marker is of suitably compact size and shape to be implanted into bone for periods of prolonged duration that may be measured in years. A cylindrical shape is preferred, as it minimizes the size of the incision required for insertion by maximizing the available volume of contrast agent for a given incision size. A permanently implanted marker allows comparison of scans over time for follow-up therapy (for example, to make lesion volume comparisons in order to monitor growth). It also allows fractionated radiotherapy, in which small doses of radiation are administered frequently over the course of treatment.

One known measure for defining known set of points about the human skull for this purpose involves the use of a stereotactic frame (see U.S. Pat. No. 4,608,977 for a general description of such a device). At present, a stereotactic frame cannot be used for this therapy because the frame poses a significant risk of infection, is too painful, or is too bulky and restrictive to be left on for an extended time and cannot be re-attached in the same location to tolerance of submillimetric accuracy. This problem is resolved by the use of an implantable marker that can be well tolerated by the patient for extended periods of time. Such an implantable fiducial marker can also be localized in the radiation therapy suite and thereby enable the patient's image space, intracranial physical space, and radiation therapy device to be registered with each other.

In another embodiment, the fiducial marker takes the form of a relatively larger temporary marker that is removably attached to a base that is rigidly affixed to bone. In this embodiment, the base portion is left in place for a period of days or weeks and is provided with means for detachably receiving an imaging marker. By permitting the removal of the imaging marker after scanning, the over-all height profile of the subcutaneous marker base is reduced, adding to its overall stability during implantation. In this way, the imaging marker, which need only be kept in place attached to its base for the few hours required for the medical procedure, can be made larger than could otherwise be tolerated in the case of markers left in place for days on end. The larger imaging marker produces a brighter image and is easier to localize in image space than would be the case for a smaller marker.

The interchangeable nature of this marker also makes it suitable for use with PET and/or SPECT scans. In both of these modalities, an image marker must be radioactive. Furthermore, in both of these modalities, it is necessary to obtain with each imaging scan a so-called "transmission scan," in which no radioactive substance is present. The transmission scan must be obtained with the patient in the same position as the imaging scan, and it is therefore not feasible for the marker bases to be implanted between scans. Instead, it is necessary to attach a nonradioactive marker for the transmission scan and then to replace the nonradioactive marker with a radioactive one for the imaging scan. The visibility of the markers in CT, MRI, PET, and SPECT images allows one to register images obtained with any of these modalities.

In both the temporary and the more permanent versions of the invention, the container is charged with aqueous imaging agents to provide imaging capability in MRI. CT imaging capability may be provided in either of two ways: by doping the plastic housing with agents that will render the marker housing imageable under CT, in which case the shape of the housing so doped is such that its volume centroid is coincident with the center of the volume occupied by the MRI imaging agent, or by mixing the aqueous MRI imaging agents with other aqueous agents imageable under CT. Additionally, both ways may be employed in the same marker. The imaging agents are selected so as to provide suitable imaging in both modalities and, where an aqueous CT imaging agent is employed, must be miscible. The use of a miscible liquid combination results in the same volume being visible in different imaging modalities with coincident centers for the purpose of locating the center of the marker. In the embodiment for PET and/or SPECT, and external marker is filled with the appropriate radioisotope and used in place of the MRI/CT markers described in the previous paragraph. In an alternative embodiment employing the temporary fiducial marker, a kit of markers can be provided in which each marker is optimized for one imaging modality (MRI, CT, PET, or SPECT).

BRIEF DESCRIPTION OF THE DRAWINGS

For a more complete understanding of this invention, reference should now be made to the embodiments illustrated in greater detail in the accompanying drawings and described below. In the drawings.

DETAILED DESCRIPTION

Referring now specifically to the drawings, wherein like numerals indicate like parts throughout, a version of a temporary fiducial marker assembly is indicated in FIGS. 1–4. These figures illustrate a fiducial marker assembly comprising an imaging marker 10 and a base 30.

Figure 3A:
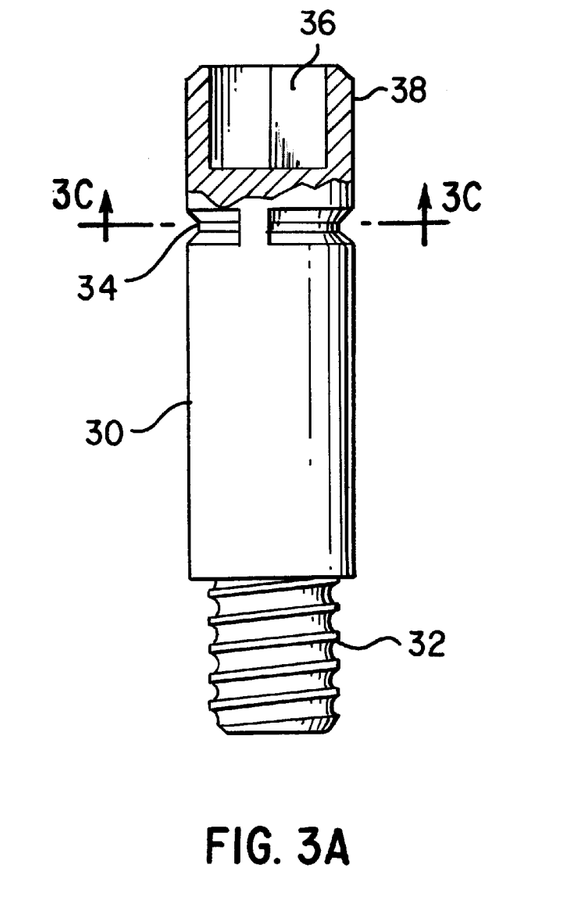
FIG. 3A is an elevational view of the base portion of the invention.
Figure 3B:
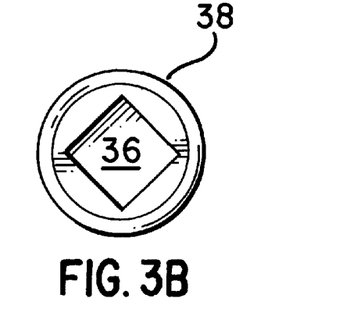
FIG. 3B is a view of the top portion of the base.
Figure 3C:
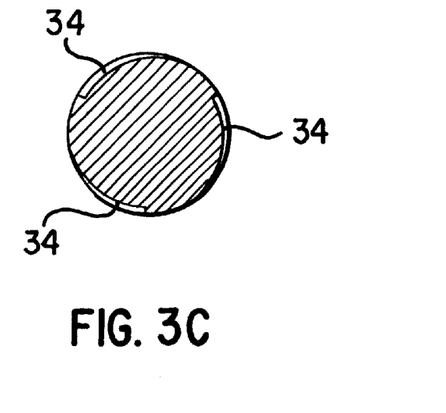
FIG. 3C is a cross sectional view of the base taken along line C—C showing the grooves that receive the imaging marker.

The base 30 has a threaded portion 32 at a first end. The threads enable a surgeon to securely attach the base into the skull or other desired portion of bone tissue. Other connecting structure is provided to securely and releasably link the imaging marker with the base. For example, in the illustrated embodiment, the end of the base opposite the threaded portion terminates in a socket head 38 which contains a socket-like recess 36. (It is anticipated that the base will be implanted into bone with the aid of an insertion tool that twists the base into the bone or into a hole provided in the bone. The recess is non-circular so as to better transmit the torque provided by such an insertion tool.) Just beneath the socket head 38 are a plurality (as seen in FIG. 3C, three) of grooves 34. As shall be further explained below, the socket 38 and the grooves 34 provide for the secure and releasable attachment of the imaging marker portion with base portion.

Figure 1A:
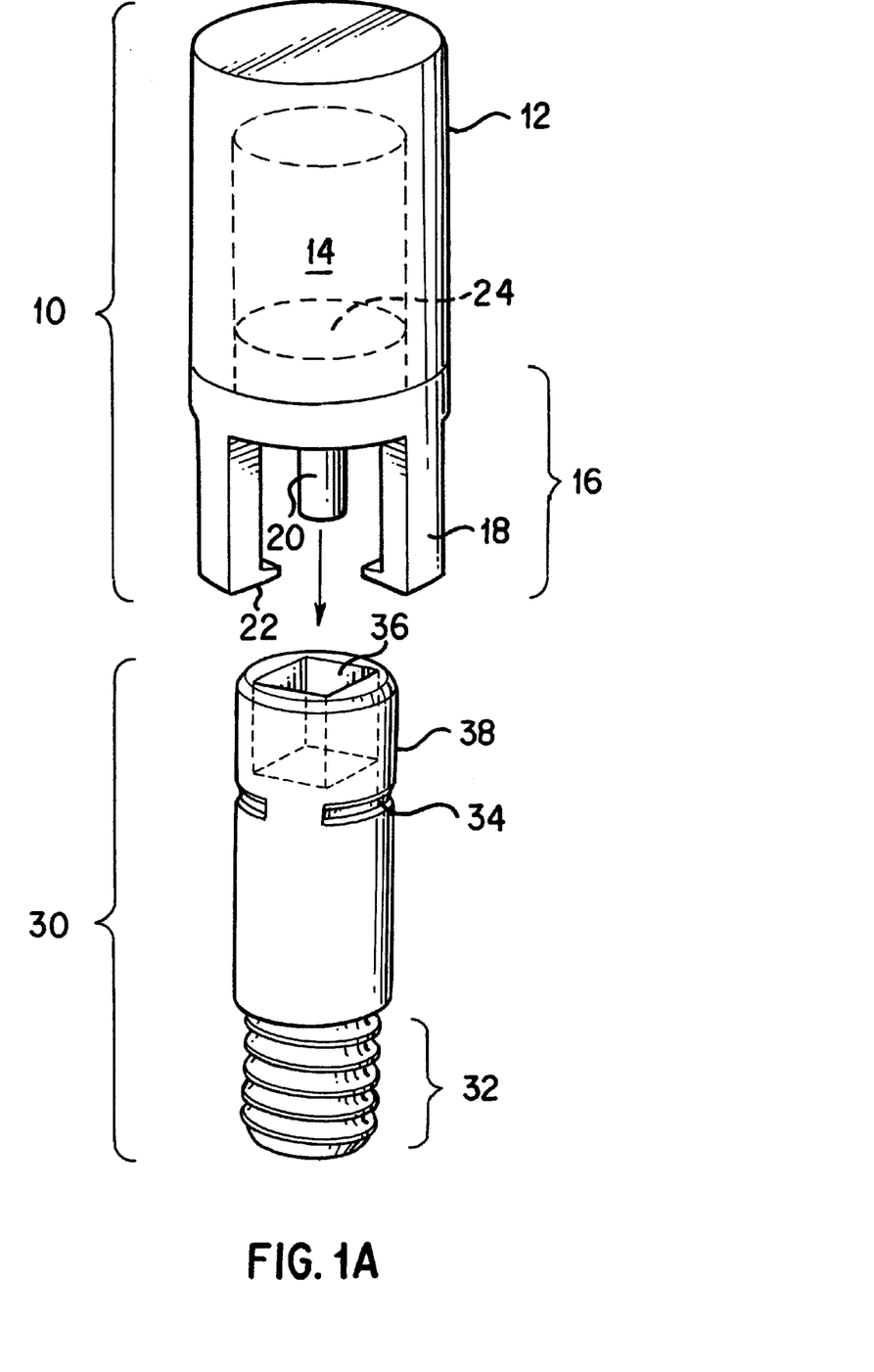
FIG. 1A is an exploded perspective view of a temporary fiducial marker embodying features of the present invention, in which the imaging marker is shown separated from the base with respect to which it can releasably be attached.
Figure 1B:
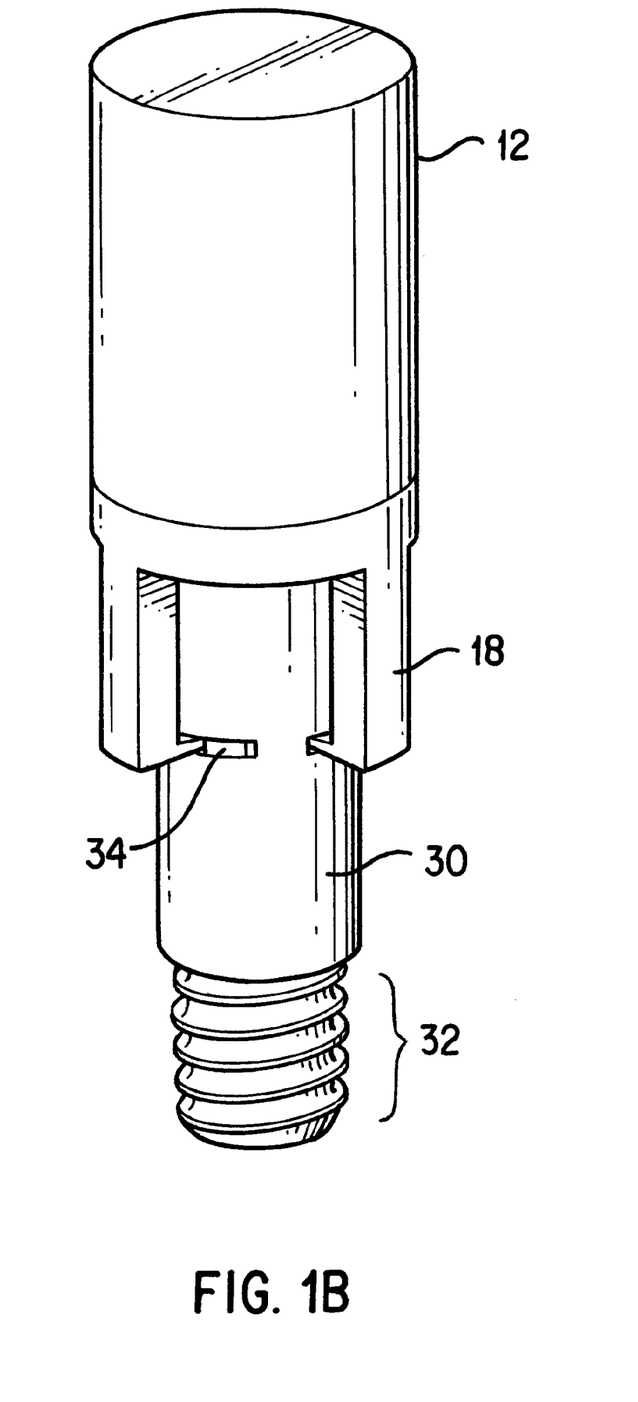
FIG. 1B shows the marker of FIG. 1a as assembled.
Figure 2A:
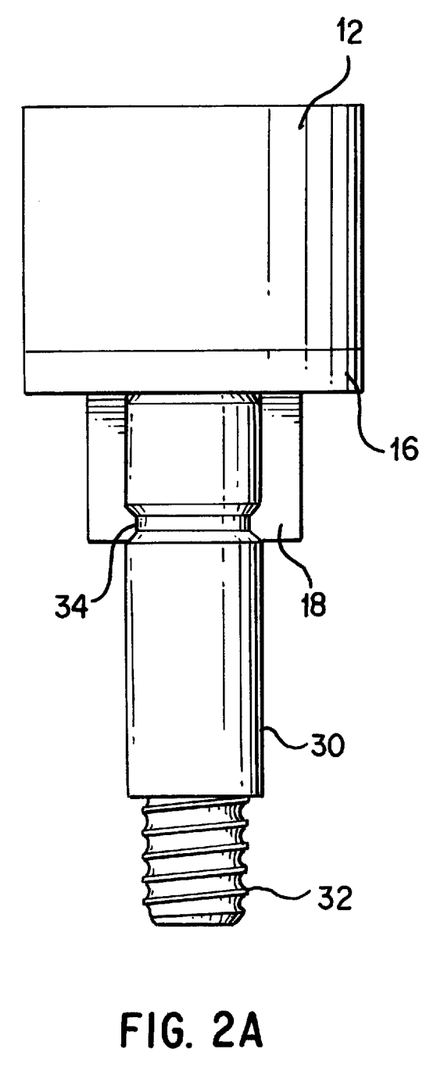
FIG. 2A is an elevational view of the fiducial marker assembly, in which the imaging marker is shown attached to the base.
Figure 2B:
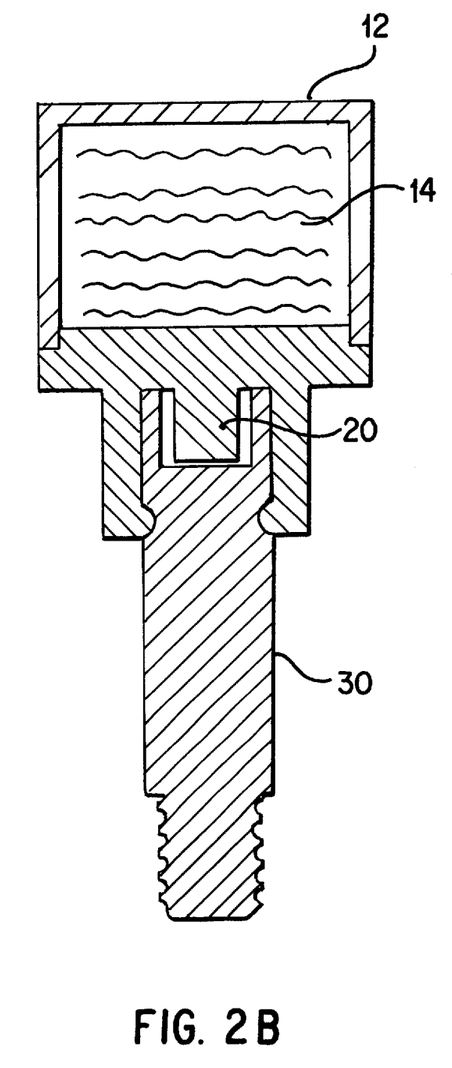
FIG. 2B illustrates in cross section the invention shown in FIG. 2A as viewed along line A—A.
Figure 4A:
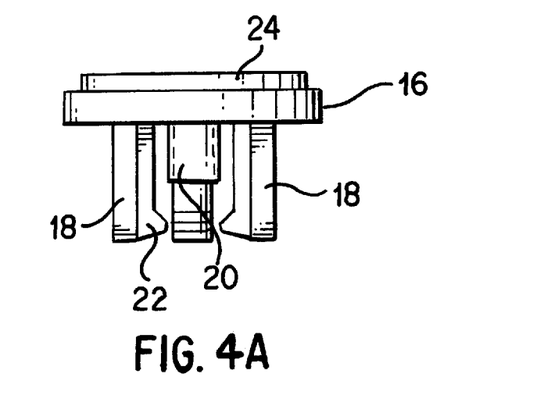
FIG. 4A is an elevational view of the cap portion of the imaging marker.
Figure 4B:
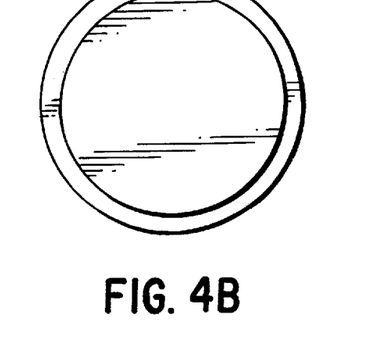
FIG. 4B is a top plan view of the cap portion shown in FIG. 4A.
Figure 4C:
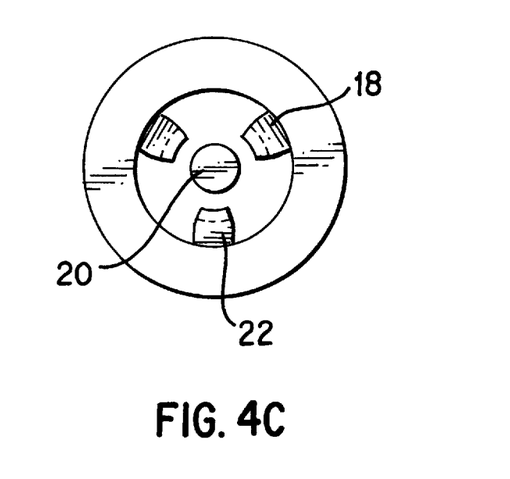
FIG. 4C is a bottom plan view of the cap.

The imaging marker portion of the temporary fiducial marker assembly may consist of two principal portions, a cylinder 12 and a cap 16 (see FIGS. 4A–4C). The cylinder 12 contains a cavity 14 for receiving a mixture of imaging agents whose composition is determined by the imaging modalities to be employed. While in this version, the vessel containing the imaging agents is preferably cylindrical so as to simplify the process by which the centroid of the corresponding volume of imaging agent is determined, other shapes (such as a box or sphere) could be employed as well. The cylinder 12 is closed at one end and open at the other to allow for the introduction of the imaging agents. In one version of the device, a cap 16 is used to seal off the open end of the cylinder once the imaging agents have been added to the cylinder. In this version, the cap may be cemented or welded into place. The cap may be provided with a plug portion 24 that protrudes into and thereby helps seal off the cavity 14 of the cylinder 12 against leakage of the imaging agents. Other conventional filling and sealing techniques, such as blow-molding, ultrasonic welding, or heat sealing, may be used.

Where a cap is employed, it may be provided with a protruding boss 20 and a plurality (here, three) of snap arms 18, which terminate with inwardly projecting portions 22. The shape and dimensions of the boss are in direct correspondence with the shape and size of the socket 36 provided in the base 30 so as to properly and securely center the imaging marker on the base. The snap arms 18 cooperate with the grooves 34 of the base 30 so as to detachably secure the imaging marker onto the base. The cooperation of these elements is illustrated in FIGS. 2a and 2b. While this example shows the use of snap arms, other fastener structure may be provided for attaching the marker to the base (e.g., screw threads, clasps, hooks, etc.).

The dimensions of the temporary fiducial marker assembly will be somewhat dependent on the state of the art of imaging. The greater the sensitivity of the scanner employed, the lesser the quantity of imaging material necessary to provide a suitable image, which in turn makes it possible to reduce the corresponding size of the marker that must be employed to contain the imaging material. The Applicants have found that a base portion approximately 12 mm in length and 2 mm–3 mm in diameter is sufficiently large to provide for the secure placement of the base into the bone beneath the skin. When the clinician prepares the patient for imaging, the base portion is exposed and an imaging marker approximately 6 mm in length is attached to the base; the marker itself may protrude from the scalp and be exposed to air while a scan is performed on the patient. The base and the imaging marker housing are constructed of a bio-compatible organic polymer, such as polyether imide.

Figure 5:
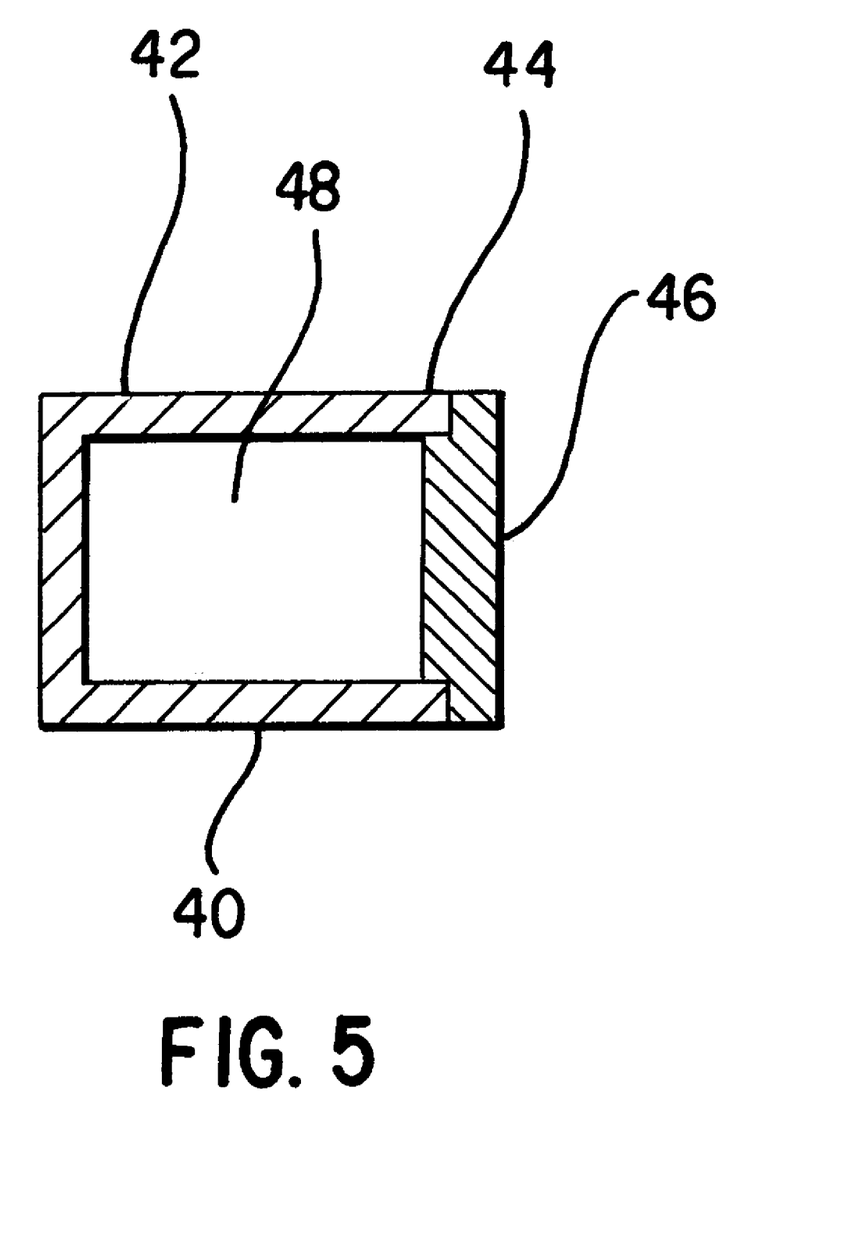
FIG. 5 is a cross sectional view of a different version of the invention.

FIG. 5 illustrates a second embodiment of the fiducial marker, which may be left implanted entirely beneath the skin for extended periods of time. The marker comprises a cylinder 42 defining a space into which is placed one or more desired imaging agents. As noted in the Summary, a cylindrical shape is preferred, because this shape minimizes the size of the incision that must be made for the marker's insertion. It is also the shape that best corresponds to the hole that one drills in the bone to accommodate the marker. The body of the cylinder is sealed off with a cap 46 or is otherwise sealed. The body is preferably constructed of an organic polymer known to be well tolerated by the body for extended periods of time, such as polymethyl methacrylate, high density polyethylene, or ceramics such as zirconium oxide and aluminum oxide. The entire marker assembly is small enough for long-term implantation into bone without causing distortion of the bone over time. One exemplary size provides for the marker to be 4 mm in length and 3 mm in diameter.

As shall be explained below, the judicious choice of aqueous imaging agents allows for the construction of a marker that is visible under both CT and MRI imaging modalities. Furthermore, by using a marker that comprises a solid outer portion and an aqueous inner portion, the marker can be located through the use of a non-invasive transcutaneous detection system, such as one employing ultrasound to detect the presence of the solid-liquid interface between the aqueous core and the solid outer portion.

Because the fiducial marker assembly is to be used in a variety of imaging modalities, the use of solid metal is eschewed throughout. The presence of metal may cause unwanted artifacts and image distortion in the image, and may impede efforts to localize the marker (i.e., locate and identify its centroid). The properties characteristic of solid metal, such as high electrical conductivity, paramagnetism, and, for some metals, ferromagnetism, are generally inappropriate for use in MRI.

Although metals have been used in the past as CT markers, they are often generally less than optimal because the high linear attenuation of metals may cause unwanted image artifacts, such as starbursts. While these artifacts can be reduced somewhat by reducing the size of the markers, this reduction in size also reduces the accuracy with which the location of the marker can be determined. In MRI, metals cause disturbances in the local magnetic field (the so-called "susceptibility" artifact) which diminish the image intensity and physically shift the position of the image. Such physical phenomena are unsuitable in a fiducial marker. The choice of materials selected as imaging agents is therefore driven by the physics underlying the image modalities that are employed.

In CT studies of human tissue, the brightest anatomical features imaged are bone, which attenuates X-rays more strongly than other tissue. This attenuation is characterized by the so-called "linear attenuation coefficient," which measures the X-ray attenuation per unit of path length. The linear attenuation coefficient increases with increasing electron density (the number of electrons per unit of volume). In order for an X-ray CT imager to produce pixels brighter than bone when imaging a material (such as that of a marker), the material being scanned must have an electron density that is greater than that of bone. Therefore, one approach to enhancing the absorption of X-rays is to increase the electron density per unit volume. This can be accomplished by adding compounds having atoms of high atomic number (Z) to the imaged object, or by substantially increasing the density of the material being scanned. Any high Z value atom suffices. Suitable materials include barium, iodine, titanium, tantalum, silver, gold, platinum, and stainless steel. These materials may be solid, or dissolved as ions in biologically compatible fluids. However, as noted above, the use of solid metal in a fiducial marker tends to create artifacts that degrade the ability of the marker to be used as a true fiducial. These artifacts are higher for markers that have higher linear attenuation coefficients. They are also higher for markers of larger sizes. In particular, for a given linear attenuation coefficient, if the shape and size of the marker is altered so that there is a longer path length through the marker, the tendency to cause an image artifact increases. It is therefore necessary to provide the high Z value material in a diluted form.

One approach to providing an imageable marker of appropriate size that does not yield unwanted artifacts is to dope the marker housing with a CT imaging agent. For example, the housing for the marker, which is normally made of organic polymers, can have barium added as a salt. Alternatively, titanium dioxide may be added to the polymeric housing. Salts of gold or of platinum are also effective materials for rendering the housing shell radio-opaque and thus imageable under CT scanning. Concentrations of these metal salts of up to about 400 mg/ml can be used in the markers without causing appreciable image artifacts. It must be born in mind that it will still be necessary to locate the geometric center of the marker housing so doped; therefore, the geometry of the doped housing should preferably be configured so that its center will be coincident with the center of the volume of any other imaging agent used to accommodate other imaging modalities.

Another approach to providing high Z value agents without resorting to the use of solid metal is to provide them in the form of an aqueous solution. Aqueous solutions of compounds having high Z atoms, such as barium, iodine, titanium, tantalum, silver, platinum, and iron can be used as imaging agents in the fiducial marker of this invention. In particular, compounds of iodine and silver have been found to be effective for this purpose.

For example, in certain preferred embodiments, an aqueous solution of an iodine containing organic molecule with an effective iodine concentration of between about 50 to about 600 mg/ml provides an effective CT imaging agent. In another preferred embodiment, silver nitrate dissolved in water at concentrations of between about 100 mg/ml to about 600 mg/ml is effective. Either solution will be effective in CT at imaging the volume defined by the marker cavity.

By judicious choice of a high-Z aqueous solution, it is possible to create a set of markers having absorption properties in X-ray CT that are anywhere between those of water and 15 times those of bone. However, the effect of these agents on MRI imaging must also be considered, as must the additional requirements that MRI imaging presents.

For example, the use of aqueous solutions where only CT imaging is contemplated is optional—other carriers, such as oils, could be used as carriers for high Z-number elements. However, this is not the case with respect to MRI. The accurate location of MRI markers in biological tissue must be done with an aqueous imaging agent. Substances other than water exhibit different resonance frequencies, or chemical shifts, and will appear in the image displaced from their true location. Therefore, where a common liquid carrier is to be used both for CT as well as MRI imaging agents, it should be water. (The phenomenon of chemical shift is further described in the literature and is well known to practitioners in the art—see e.g., "Edge Artifacts in MR Images: Chemical Shift Effect," *Journal of Computer Assisted Tomography* 9(2):252–257 (1985).)

The physics of MRI scanning must further be considered. Pure water is characterized in proton nuclear magnetic resonance by a high spin density and long T1 and T2 values. The relaxation times are in the range of two to four seconds. MRI images are partly based on spin density as well as T1 and T2. The effect of spin density on image brightness is linear; reducing the spin density by one half reduces the brightness by one half. The effects of T1 and T2 are exponential; for example, altering these by one half results in a change of 86% in the brightness in the image. These factors may be summarized mathematically as follows:

$$I = NC(e^{-(TE/T2)})(1-e^{-(TR/T1)})$$

where I=signal intensity, N=spin density, the parameters TR and TE are the repetition time and the echo time determined by the radio frequency and gradient pulses employed, and C is a constant of proportionality that depends on the scanner and the pulses employed.

These three parameters, T1, T2, and spin density, can be altered by the addition of chemicals selected for their physical properties in solution. One such property is paramagnetism, in which the added material has an unpaired electron in its electron configuration. Such agents shorten the relaxation times T1 and T2 drastically. Another such property is viscosity. Other chemicals may be added to the solution for their ability to alter the viscosity of a solution, even to a point of making a gel. Viscosity is an important consideration, because it is inversely correlated with T2. The more viscous a solution, the greater the number of bonds that are present and the less able the hydrogen nuclei are to react and respond to the magnetic field, which results in a dimmer image. These viscosity enhancing agents dilute the water in the solution, thereby reducing the spin density, and reduce the relaxation times T1 and T2. Whatever the added material, T1 will always be equal to or greater than T2.

Because of the small concentrations of MRI imaging agents appropriate for MRI enhancements, these agents have no significant effect on the CT imaging agent. However, the efficacy of an MRI imaging agent may be obscured by the presence of a CT imaging agent. The MR image is modulated by the cumulative effects of all solutes added to an aqueous medium. This modulation is due to interactions with the hydrogen atoms in water which provide the MR signal. The general effects of three typical CT imaging agents, of one typical MR imaging agent, and of selected combinations of these two types of agents are presented below.

In accordance with the above discussion, it has been determined that silver nitrate, which, as noted above, provides a suitable image under CT scans when provided in concentrations up to about 600 mg/ml, reduces the observed spin density (and hence reduces the brightness of the MR image) by up to 50%. At a preferred concentration of about 600 mg/ml, the observed T1 and T2 values are about 1 second. As the concentration of silver nitrate decreases, the T1 and T2 values approach those of pure water. This observed effect affords the opportunity to provide a variety of marker compositions based on silver nitrate (as the CT agent) to create differing contrast levels with respect to human tissue under MRI.

A solution of iohexol (a non-ionic X-ray CT imaging agent) in concentrations of up to about 600 mg/ml of iodine also reduces the observed spin density by up to 50%. At a concentration of 150 mg of iodine per ml of aqueous solution, the observed T1 value is 300–400 milliseconds, and the observed T2 value is 100–120 milliseconds. The effect on these parameters is in accord with similar effects noted from increasing the viscosity of aqueous solutions. Over the entire range of iohexol concentrations, it has been determined that one can alter the spin density by 50%, change the T1 value from 4 seconds to 0.15 seconds, and the T2 value from 4 seconds to 0.04 seconds. Thus, iohexol too, may be used to provide a variety of marker compositions to create different contrast levels with respect to human tissue under MRI.

A solution of iothalamate meglumine (an ionic X-ray CT imaging agent) in concentrations up to about 600 mg/ml of iodine reduces the observed spin density by factors ranging up to 75%. At a concentration of 175 mg of iodine per ml of aqueous solution, the observed T1 value is 1200–1500 milliseconds, and the observed T2 value is 300–350 milliseconds. The solution is not viscous at this concentration. Over the entire range of iothalamate meglumine concentrations it has been determined that one can alter proton spin by 75%, change T1 value from 4 seconds to 1 second, and the T2 value from 4 seconds to 200 milliseconds. Thus iothalamate meglumine may be used to provide a variety of marker compositions to create different contrast with respect to human tissue.

Within limits, one can prepare solutions of reduced spin density in which T1 is equal to T2, and solutions providing spin density in which T1 is greater that T2. T1 and T2 values of these altered solutions range from 1 millisecond to 4 seconds, while the spin density ranges from 0 molar (no water at all) to 111 molar in hydrogen (pure water). The instant invention identifies a number of substances suitable for use in MRI imaging in fiducial markers. One preferred suitable MRI imaging agent is gadopentetate dimeglumine. Another possible MRI imaging agent is gadoteridol. (Each of the aforementioned substances has received FDA approval for use as an injectable MRI imaging agent.) Other possible agents for use as MRI imaging agents include Ferric Chloride ($FeCl_3$) and Copper Sulfate ($CuSO4$) in concentrations of between 0.5 mM and 5 mM. For a more complete listing of contrast agents and their properties, see chapter 14 of *Magnetic Resonance Imaging*, 2nd ed., edited by Stark and Bradley, 1992, the contents of which are herein incorporated by reference.

A solution of gadopentetate dimeglumine-DPTA (an injectable MR contrast agent) in concentrations up to about 0.5 mM (millimolar) is seen to have little effect on the observed spin density of the solution. At a concentration of 0.5 mM, the observed T1 value is 50 to 100 milliseconds, and the observed T2 value is 8 to 15 milliseconds. Over the entire range of concentrations one observes spin density of 111 molar in hydrogen (water). T1 varies from 50 milliseconds to 4 seconds, and T2 varies from 8 milliseconds to 4 seconds. This is in accord with the reported effect of the paramagnetic material. By varying the marker compositions based on the gadopentetate compound, it is possible to create a variety of different contrasts with respect to human tissue.

The four solutions just discussed were based on one solute in water. To provide a multi-modality marker, binary mixtures of CT and MR contrast agents are considered. It has been observed that binary combinations of gadopentetate-DPTA with any of the other chemical compounds set forth produce a synergistic effect. The matrix of possibilities for altering spin density, T1 and T2, by varying the concentration of MRI and CT imaging agents, enhances the ability to tailor solutions to give maximum contrast in all three types of MR image parameters. For example, with respect to the permanent marker, iothalamate meglumine at a concentration of 175 mg/ml combined with gadopentetate meglumine-DPTA at 0.5 mM creates a solution with the following MR properties: a spin density corresponding to 75–80 molar water, T1 value of 400–500 milliseconds, and a T2 value of 150–200 milliseconds. A variety of other binary compositions permit one to create many different ratios of spin density, T1 and T2 values.

Hence, as these examples suggest, it is possible to create a set of MR markers with any combination of spin density, T1 and T2 that are smaller in magnitude than those of water. The optimum values of these parameters as specified by the marker application dictate the composition of the solution.

For one marker to be optimized for both MRI and CT, the imaging agents and their concentrations must be selected such that the solution and/or housing may be differentiated in the X-ray by its radio-opacity and at the same time be differentiated in the MRI by its MRI parameter set—spin density, T1, and T2. As noted above, it is known that aqueous solutions of compounds based on high Z number elements will provide the necessary degree of radio-opacity for CT imaging. It is also known that such substances may reduce the imaging efficacy of compounds selected for their use as MRI contrast agent, such as gadopentetate dimeglumine-DPTA. In order to combine the two agents in an effective manner, they are mixed together in varying concentration and tested under both CT and MRI scans until one has empirically determined a concentration of each that provides a marker that is acceptably imageable under both modalities.

As a result of such a course of testing, the Applicants have identified two preferred binary mixtures that meet these requirements when used in the permanent marker; these are iothalamate meglumine (175 mg of iodine/ml) with gadopentetate dimeglumine-DPTA (0.5 mM) and silver nitrate (350 mg/ml) with gadopentetate dimeglumine-DPTA (0.5 mM). In the case of the temporary marker, the concentrations of the CT imaging agents are reduced to 165 mg of iodine per ml of aqueous solution of iothalamate meglumine and 200 mg/ml of silver nitrate respectively.

The present invention may be embodied in other specific forms without departing from its spirit or essential characteristics. For example, the aqueous solutions used as the carrier for the imaging agents could have the characteristics of a gel. The imaging agents could be provided as mixtures of three or more compounds selected to optimize particular imaging characteristics.

The present invention may be embodied in other specific forms without departing from its spirit or essential characteristics. For example, a flatter, more disk-like marker than that which is shown in the figures may be employed. Increasing the largest dimension of X-ray traversal boosts the brightness of the image in CT. It also allows one to take CT scans with thicker slices in which the image of the marker does not become lost in the corresponding pixel. This is especially useful in trauma cases, when there is not sufficient time for more refined views.

In another variant, the imaging agents discussed above can be relied upon for one imaging mode and another technique relied on for locating the marker in a second imaging mode. For example, one may image a marker under a first modality (e.g., MRI) using the imaging agents discussed above, and then locate the marker in the image space generated by a second imaging modality (e.g., CT) by physically locating the marker in the physical space of the second imaging machine. For example, robotic arms such as are disclosed in U.S. Pat. No. 5,142,930 (the contents of which are herein incorporated by reference) or U.S. Pat. No. 4,991,579 could be used for this purpose, since in the course of a scan the addresses of each point in image space are generally defined with respect to the imaging machine and hence to any arm (such as that disclosed in the '930 patent) or other device whose location is clearly defined with respect to that machine. One may then label the corresponding point in image space as containing the location of marker, even where it is not directly imageable in that imaging mode.

What is claimed is:

1. A fiducial marker system, comprising:
   a) a base adapted to be affixed to the anatomy; and
   b) a fiducial marker adapted to be releasably attached to the base, the fiducial marker further comprising an imaging agent imageable in both X-ray computed tomography (CT) images and magnetic resonance (MR) images;
   c) wherein the imaging agent does not cause image distortion or artifacts in CT images; and
   d) wherein the imaging agent does not cause image distortion or artifacts in MR images.

2. The fiducial marker system of claim 1, wherein the base is adapted to be affixed to bone.

3. The fiducial marker system of claim 1, wherein the fiducial marker does not include metal.

4. The fiducial marker system of claim 1, wherein the imaging agent is an aqueous imaging agent.

5. The marker of claim 4, wherein the imaging agent further comprises a high Z-value agent that renders the marker imageable in a computed tomographic image.

6. The marker of claim 5, wherein the high Z-value agent is selected from the group consisting of barium, iodine, titanium, tantalum, silver, platinum and iron.

7. The marker of claim 6, wherein the material further comprises an aqueous solution of iothalamate meglumine and gadopentate dimeglumine-DPTA.

8. The marker of claim 7, wherein the gadopentate dimeglumine-DPTA is present in a concentration of about 0.5 mM.

9. The marker of claim 7, wherein the iothalate meglumine is present in a concentration of about 50 to 600 mg iodine per ml of solution.

10. The marker of claim 6, wherein the material further comprises an aqueous solution of silver nitrate and gadopentate dimeglumine-DPTA.

11. The marker of claim 10, wherein the gadopentate dimeglumine-DPTA is present in a concentration of about 0.5 mM.

12. The marker of claim 10, wherein the silver nitrate is present in a concentration of about 100 to 600 mg silver nitrate per ml of solution.

13. A fiducial marker, comprising:
    a) a housing adapted to contain an imaging agent; and
    b) an imaging agent contained within the housing, wherein the imaging agent is imageable in both X-ray computed tomography (CT) images and magnetic resonance (MR) images;
    c) wherein the imaging agent does not cause image distortion or artifacts in CT images; and
    d) wherein the imaging agent does not cause image distortion or artifacts in MR images.

14. The fiducial marker system of claim 13, wherein the fiducial marker does not include metal.

15. The fiducial marker system of claim 13, wherein the imaging agent is an aqueous imaging agent.

16. The marker of claim 15, wherein the imaging agent further comprises a high Z-value agent that renders the marker imageable in a computed tomographic image.

17. The marker of claim 16, wherein the high Z-value agent is selected from the group consisting of barium, iodine, titanium, tantalum, silver, platinum and iron.

18. The marker of claim 17, wherein the material further comprises an aqueous solution of iothalamate meglumine and gadopentate dimeglumine-DPTA.

19. The marker of claim 18, wherein the gadopentate dimeglumine-DPTA is present in a concentration of about 0.5 mM.

20. The marker of claim 18, wherein the iothalate meglumine is present in a concentration of about 50 to 600 mg iodine per ml of solution.

21. The marker of claim 17, wherein the material further comprises an aqueous solution of silver nitrate and gadopentate dimeglumine-DPTA.

22. The marker of claim 21, wherein the gadopentate dimeglumine-DPTA is present in a concentration of about 0.5 mM.

23. The marker of claim 21, wherein the silver nitrate is present in a concentration of about 100 to 600 mg silver nitrate per ml of solution.

* * * * *

UNITED STATES PATENT AND TRADEMARK OFFICE
CERTIFICATE OF CORRECTION

PATENT NO. : 6,333,971 B2  Page 1 of 1
DATED : December 25, 2001
INVENTOR(S) : McCrory et al.

It is certified that error appears in the above-identified patent and that said Letters Patent is hereby corrected as shown below:

Title page,
Change the "Related U.S. Application Data" to read as follows: -- [62] Division of application No. 08/480,709, filed on 7 June 1995, which is a continuation of application No. 08/017,167 filed 12 February 1993, abandoned. --

Column 6,
Line 24, change "the-shape" to -- the shape --.

Column 9,
Line 54, change "CuS04" to -- $CuSO_4$ --.

Signed and Sealed this

Twenty-first Day of May, 2002

Attest:

Attesting Officer

JAMES E. ROGAN
Director of the United States Patent and Trademark Office